(12) United States Patent
Ausborn et al.

(10) Patent No.: US 8,110,224 B2
(45) Date of Patent: Feb. 7, 2012

(54) PHARMACEUTICAL MICROPARTICLES

(75) Inventors: Michael Ausborn, Lorrach (DE); Olivier Lambert, Spechbach-le-Haut (FR); Oskar Nagele, Sissach (CH)

(73) Assignee: Novartis AG, Basel (CH)

( * ) Notice: Subject to any disclaimer, the term of this patent is extended or adjusted under 35 U.S.C. 154(b) by 455 days.

(21) Appl. No.: 12/218,639

(22) Filed: Jul. 17, 2008

(65) Prior Publication Data

US 2008/0279955 A1 Nov. 13, 2008

Related U.S. Application Data

(63) Continuation of application No. 10/506,822, filed as application No. PCT/EP03/02565 on Mar. 12, 2003, now abandoned.

(30) Foreign Application Priority Data

Mar. 13, 2002 (DE) .................. 102 11 040
Mar. 27, 2002 (DE) .................. 102 13 856

(51) Int. Cl.
*A61K 9/14* (2006.01)
(52) U.S. Cl. ...................................................... 424/489
(58) Field of Classification Search .................. None
See application file for complete search history.

(56) References Cited

U.S. PATENT DOCUMENTS

| 5,593,687 | A | | 1/1997 | Rossling et al. | ............. 424/450 |
| 5,718,922 | A | * | 2/1998 | Herrero-Vanrell et al. | ... 424/501 |
| 5,948,441 | A | * | 9/1999 | Lenk et al. | ..................... 424/489 |
| 2002/0114835 | A1 | * | 8/2002 | Sackler et al. | ................ 424/468 |

FOREIGN PATENT DOCUMENTS

| EP | 0 400 522 | | 12/1990 |
| EP | 0 418 153 | | 3/1991 |
| EP | 0 474 098 | | 3/1992 |
| EP | 0 998 917 | | 5/2000 |
| EP | 1 277 787 | | 1/2003 |
| WO | 00/03660 | | 1/2000 |
| WO | 00/56282 | | 9/2000 |
| WO | WO0056282 | * | 9/2000 |
| WO | 01/83594 | | 11/2001 |

* cited by examiner

*Primary Examiner* — Bethany Barham
(74) *Attorney, Agent, or Firm* — Carmella A. O'Gorman

(57) ABSTRACT

Microparticles consisting of (a) a matrix with a mixture of (a1) at least one hydrophobic, biologically degradable polymer and (a2) optionally at least one water-soluble polymer, (b) a pharmaceutical active ingredient distributed in the matrix, and (c) in addition at least one water-insoluble, surface-active substance from the group of lecithins and phospholipids, distributed in the matrix, and a three-phase emulsion process for their preparation.

23 Claims, No Drawings

PHARMACEUTICAL MICROPARTICLES

This is a continuation of application Ser. No. 10/506,822 filed on Sep. 7, 2004, which is National Stage of International Application No. PCT/EP03/02565 filed on Mar. 12, 2003, the entire disclosures of which are hereby incorporated by reference.

The invention relates to microparticles comprising at least one biologically degradable polymer, optionally at least one water soluble polymer and at least one pharmacologically active ingredient distributed in the polymer containing a phospholipid or lecithin and a process for their preparation.

Microparticles comprising a mixture of a biologically degradable polymer and a water-soluble polymer, into which a pharmaceutical active ingredient, preferably peptides, polypeptides or proteins, are incorporated, are known from U.S. Pat. No. 5,869,103. It is mentioned that an undesired initial high release of active ingredient, especially surface-active proteins, may be suppressed if, during production of the particles, a stabiliser, for example surfactants such as sorbitan monostearate or glyceryl monostearate, is added to the organic phase of an active ingredient emulsion or suspension. When active ingredient is released in contact with a physiological medium, such surfactants are washed out particularly quickly, so that the microparticle composition changes. Therefore, these surface active agents will stay in the polymer matrix for a very short period and will not prevent a possible adsorption of the drug substance to the polymer matrix during the release period. Therefore, a release of active ingredient over a longer period is not achieved.

In Pharmaceutical Research, Vol. 14, No. 4, pages 420 to 425 (1997), J. L. Cleland describes the encapsulation of a recombinant human growth hormone with a biologically degradable polymer, for example a copolycondensate comprising lactic acid and glycolic acid. In this system, the initial high release of active ingredient can only be reduced, and the possible denaturing of the hormone is avoided by adding trehalose or mannitol.

In Biotechnology and Bioengineering, Vol. 65, No. 6, pages 659 to 667 (1999), H. K. Tim et al describe that the encapsulation of the recombinant human growth hormone in a copoly-condensate comprising lactic acid and glycolic acid leads to systems which have a high initial release of hormone of up to over 50% and afterwards no longer release any active ingredient. M. Morlock et al. [European Journal of Pharmaceutics and Biopharmaceutics 43 (1997), pages 29-36] and 8. Sittner et al. [European Journal of Pharmaceutics and Biopharmaceutics 45 (1998), pages 295-305] describe a similar behaviour when recombinant human erythropoietin is encapsulated in a copolycondensate of lactic acid and glycolic acid.

The problem of encapsulating pharmaceutical active ingredients, especially surface-active peptides, polypeptides and proteins in biologically degradable polymers, in order to attain a constant release of active ingredient over a longer period of time without a loss of activity in production and during storage and administration, has not yet been solved in a satisfactory manner.

It has now surprisingly been found that, using at least one water insoluble surface active substance from the group of lecithins and phospholipids together with the polymer for the preparation of microparticles, high concentrations of pharmacologically active ingredient in the area of the surface of microparticles may be avoided. The continuous release may last at least over a long period of time without observing a complete breakdown of pharmacologically active ingredient into the surrounding biological medium.

In one aspect the invention provides microparticles comprising
 a) at least one biologically degradable polymer, and
 b) optionally at least one water soluble polymer, and
 c) at least one pharmacologically active ingredient distributed in the polymer
 d) containing a phospholipids or lecithin The microparticles may have an irregular and preferably essentially spherical shape. The particle diameter of the individual microparticles may be 0.1 to 200 µm, preferably 1 to 100 µm, most preferably 1 to 50 µm. Microparticles having an average particle diameter in the range of 5 to 80 µm, preferably 30 to 70 µm, are preferred. The particle size may be controlled, for example, by adjusting the process parameters and by selecting solvents, polymers and the molecular weight of the polymers employed.

Depending on the preparation process and the composition, the microparticles may be compact and essentially pore-free particles, or porous particles with a compact or porous surface.

As used herein "biologically degradable polymers" means for example those polymers that are decomposed in a physiological medium. Hydrolytically degradable polymers are basically appropriate for this.

Biologically degradable polymers are known and are, in part, commercially obtainable. They may be, for example homo- or copolyesters of dicarboxylic acids, alkylene diols, polyalkylene glycols and/or aliphatic hydroxycarboxylic acids; homo- or copolyamides of dicarboxylic acids, alkylene diamines, and/or aliphatic aminocarboxylic acids; corresponding polyester-polyamide copolymers, polyanhydrides, polyorthoesters, polyphosphazenes and polycarbonates. Suitable dicarboxylic acids are, for example, terephthalic acid and especially saturated aliphatic acids of formula HOOC—$(C_nH_{2n})$—COOH, wherein n is 0 or a number from 1 to 6 (oxalic, malonic, succinic or adipic acid). Alkylene diols may correspond for example to HO—$(C_xH_{2x})$—OH, wherein x is a number from 1 to 6 (ethane-, propane-, butane-, pentane- or hexanediol). The hydroxycarboxylic acids may correspond to formula HO—$(C_xH_{2x})$—COOH, wherein x is a number from 1 to 6 (hydroxyacetic acid, hydroxypropionic acid, hydroxybutanoic acid, hydroxypentanoic acid, hydroxyhexanoic acid). The aminocarboxylic acids may correspond to formula $H_2N$—$(C_xH_{2x})$—COOH, wherein x is a number from 1 to 6 (aminoacetic acid, aminopropionic acid, aminobutanoic acid, aminopentanoic acid, aminohexanoic acid). The polyalkylene glycols in question may be, for example, oligomers of ethylene glycol or propylene glycol with ca. 2 to 100, preferably 2 to 50 monomer units. Polycarbonates may contain recurring structural elements of formula —CO—$(C_xH_{2x})$—O—, wherein x is a number from 1 to 6. The molecular weight of the polymers may be, for example, 500 to 1,000,000, preferably 1000 to 500,000, most preferably 2000 to 100,000 daltons.

The biologically degradable polymers may be linear, branched and optionally crosslinked. According to the invention, star polymers may also be used, in which polymer chains are bonded to the functional groups (for example hydroxyl, amino and/or carboxyl groups) of a core monomer, such as saccharides. Such polymers are known and are partly commercial.

Preferred biologically degradable polymers are selected from the group of polycarbonates, and in particular the polyesters and polyamides of aliphatic hydroxycarboxylic acids or aminocarboxylic acids. Homo- and copolycondensates of α-hydroxycarboxylic acids are especially preferred, for example glycolic acid and lactic acid. The ratio of monomers in copolycondensates may be, for example, 10:1 to 1:10, preferably 1:4 to 4:1. Especially preferred polycondesates are poly-L- or poly-D,L-lactic acid. Preferred copolycondensates are poly-D,L-lactide/glycolides with a monomer ratio of ca. 1:1 and a molecular weight of 5000 to 100,000 daltons. Mixtures of biologically degradable polymers may also be used. The biologically degradable polymers are essentially insoluble in water.

Water-soluble polymers are likewise known and available commercially. They may be, for example, homo- or copoly-oxa-alkylene oxides of preferably ethylene and/or propylene glycol, polyacrylamides and hydroxyalkylated polyacrylamides, polymaleic acid and the partial esters or amides thereof, polyacrylic acid and the partial esters or amides thereof, polyvinyl alcohol and the partial esters or ethers thereof, polyvinyl imidazole, polyvinyl pyrrolidone, and natural polymers, for example starch or chitosan. Polyvinyl pyrrolidone is preferred. The water-soluble polymers may have molecular weights of 1000 to 500,000, preferably 1000 to 100,000, most preferably 1000 to 20,000 daltons. Mixtures of water-soluble polymers may also be used. The water-soluble polymers should also be soluble in organic solvents.

The amount of biologically degradable polymers may be, for example, 99 to 1% by weight, preferably 90 to 50% by weight, and the amount of water-soluble polymers may be 1 to 99% by weight, preferably 10 to 50% by weight, based on the composition of the polymers.

The microparticles contain at least one water-insoluble surfactant from the group of lecithins and phospholipids, the addition of which ensures that the active ingredient is protected against adsorption on the polymer matrix during the whole release period. Due to this effect the invention provides microparticles with extended release of an active ingredient. Lecithins and phospholipids are known and are available commercially. These surfactants may be extracted from natural products such as eggs or soya. The lecithins in question are natural, partly hydrogenated and hydrogenated lecithins or sphingolipids. Natural lecithins are mixtures of different phospholipids. Examples of phospholipids are phosphatidyl choline, phosphatidyl ethanolamine, lysophosphatidyl choline, phosphatidyl glycerine, phosphatidic acid and phosphatidyl serine, as well as the partially or fully hydrogenated derivatives thereof. Examples of phospholipids with defined fatty acids are 1,2-dimyristoyl-sn-glycero-3-phosphocholine, 1,2-dipalmitoyl-sn-glycero-3-phosphocholine, 1,2-distearoyl-sn-glycero-3-phosphocholine, 1,2-dioleoyl-sn-glycero-3-phosphocholine, 1-palmitoyl-2-oleoyl-sn-glycero-3-phosphocholine, 1,2-dimyristoyl-sn-glycero-3-phospho-rac-glycerine, 1,2-dipalmitoyl-sn-glycero-3-phospho-rac-glycerine and 1,2-distearoyl-sn-glycero-3-phospho-rac-glycerine. Lecithin and phosphatidyl choline are preferably used.

The amount of lecithins and/or phospholipids may be 0.01 to 90% by weight, preferably 0.1 to 70% by weight, most preferably 0.1 to 20% by weight, based on the total composition of the microparticles. The lecithins and phospholipids are essentially uniformly distributed throughout the volume of the microparticles. Insofar as the lecithins or phospholipids are only partly soluble or insoluble in the solvent of the polymer solution, the formation of a dispersion of these substances in the polymer solution may be sufficient to achieve the effects according to the invention.

The pharmacologically active ingredients are in general those that are stable under the preparation conditions. Water-soluble active ingredients are preferred. Peptides, polypeptides and proteins are preferred according to the invention, especially those which adhere to the surface of microparticles because of their surface-active properties and lead to the formation of agglomerates. Further examples are carbohydrates, oligonucleotides, RNA and DNA. A few examples of peptides, polypeptides and proteins are antibodies, growth hormones, insulin, interferons, erythropoietin, calcitonin, heparin, somatostatins, cell-stimulating factors and parathyroid hormones. The aqueous solutions may contain buffers and electrolytes, for example NaCl. Examples of interferons are interferons of the alpha group, preferably interferon alpha 2a or alpha 2b, most preferably interferon alpha 2b.

The amount of active ingredient in the microparticles may be 0.1 to 90% by weight, preferably 1 to 70% by weight, most preferably 1 to 20% by weight, based on the weight of the microparticles.

Preparation processes for microparticles are known per se and are described in relevant literature. According to the invention, the water-insoluble and surface-active substances are hereby added to the polymer solution, thereby providing optimum protection of the pharmacologically active ingredients during encapsulation and good distribution of the substance in the polymer of the microparticles.

The particles may be produced, for example by dispersing solid active ingredients or emulsifying liquid active ingredients or active ingredient solutions in physiologically compatible solvents in a polymer solution containing at least one surface-active substance, and subsequently removing the solvent. Evaporation may be undertaken at high agitation speeds in order to form the particles. It is expedient to carry out spray-drying.

Microparticles may also be produced by precipitating the polymer through the addition of a solvent, in which a polymer is insoluble, at high agitation speeds, whereby the pharmacologically active ingredient or the solution of an active ingredient is embedded in the polymer of the formed microparticles.

In another aspect the invention provides a method of producing microparticles by forming polymers from polymer precursors (for example monomers and/or prepolymers) in a dispersion or emulsion of an active ingredient or active ingredient solution with the polymer precursors at high agitation speeds. Dispersed or emulsified pharmacologically active ingredient is hereby coated and precipitated by separating the polymer.

In a further aspect of the invention microparticles may be formed by using encapsulation by means of polymer separation in multi-phase systems of aqueous and organic media, which are similarly known. For example, it is possible to emulsify aqueous solutions, dispersions or emulsions of active ingredient in an organic polymer solution, and then to emulsify this emulsion in turn in water, in order to then form the microparticles by removing the solvent. Furthermore, solutions, dispersions or emulsions of active ingredient in an organic solvent can also be emulsified in water, this emulsion is then emulsified in an organic polymer solution, and afterwards the polymer is then precipitated by adding a solvent which is immiscible with the polymer solution.

The water-insoluble and surface-active substances are hereby added to the polymer solution, thereby providing optimum protection for the active ingredients during encapsulation, with good distribution of the substance in the polymer of the microparticles.

Water-soluble pharmacologically active ingredients and in particular water-soluble, optionally surface-active peptides, polypeptides and proteins are preferably used as the aqueous formulation for encapsulation, whereby it is particularly advantageous to form the microparticles in a three-phase system.

A further object of the invention is a process for the preparation of microparticles, comprising the steps
- a) preparation of an aqueous solution e.g. a phosphate buffer of at least one pharmacologically active ingredient
- b) preparation of a solution of a biodegradable polymer and optionally a water soluble polymer as well as a surface active substance e.g. a phospholipid or lecithin in an organic solvent which is insoluble in water e.g. methylenechloride.
- c) mixing a surfactant e.g. polyvinyl alcohol with phosphate buffer to form an aqueous solution
- d) mixing solution a) and b) using a gear pump to form an emulsion
- e) pumping emulsion d) and the aqueous solution c) with a gear pump to a static mixer and mixing them in the static mixer to form a water in oil in water emulsion
- f) removing e.g. evaporating the solvent from emulsion e)
- g) separating the microparticles by sedimentation (optionally by filtration) and freeze-drying Depending on the solubility of the pharmacologically active ingredient and the desired dosaging thereof, the aqueous solution of process step a) may contain 0.01 to 80%, preferably 0.1 to 60%, most preferably 0.1 to 30% by weight of pharmacologically active ingredient, based on the aqueous solution. The solution may contain stabilising agents and/or water-soluble thickeners. If peptides, polypeptides or proteins are used, it is expedient to add pH buffers, e.g. phosphate buffers. In the case of peptides, polypeptides or proteins, it is also advantageous to add protecting agents, for example glycine or sugar. The components may be mixed and dissolved by stirring, optionally whilst heating. Any insoluble constituents can be filtered off before further use.

The polymers and the surface-active substance are conveniently dissolved whilst stirring, optionally with heating. Any insoluble constituents can be filtered off before further use. The amount of biologically degradable polymer in the solution may be, for example, 1 to 60%, preferably 0 to 50% by weight, the amount of water-soluble polymer 0 to 50% by weight, and the amount of surface-active substance 1 to 80%, preferably 2 to 40% by weight, whereby the percentages by weight add up to 100%. Suitable solvents, which are immiscible with water, are for example hydrocarbons, halogenated hydrocarbons and ketones. Preferred solvents are halogenated hydrocarbons, for example chloroform, ethane trichloride or tetrachloride, and in particular methylene dichloride.

In order to form an emulsion of the active ingredient solution (a) in the solution of polymers and surface-active substances (b), the solutions are mixed by agitating at high speed. The volume ratio of solution a) to solution b) may be, for example, from 1:1 to 1:50, preferably from 1:2 to 1:10. We have found out that this emulsion forming step may be carried out in a particularly advantageous manner by using a gear pump.

Gear pump technology is well known. Rotary gear pump may be based on meshing gears. Gear pumps are positive displacement pumps utilizing a set of gears as the displacement device. The fluid pumps may have e.g. helical gears (angled teeth), spur gears (straight teeth), or herringbone gears.

A typical gear pump includes at least two and sometimes at least three gears including a drive gear and a driven gear housed within a pumping chamber. Gear pumps are preferred by the present applicants because of their quiet operation, hydraulic efficiency, conjugate mechanical motion, constant sealing of the surfaces between the mating gear flanks and the minimum entrapment of fluid between the teeth that are in contact. The gear pump may have a high load carrying capacity and run more smoothly.

The gear pump may be based on cavity technology. Such gear pumps typically consist of a housing having an inlet, a liquid conduit and an outlet. In the housing is a gear cavity, within which gears meshingly engage and rotate. Liquid enters the gear cavity near the engagement of the gears and on a side wherein the gear teeth are disengaging. As liquid enters the gear cavity it is entrained between the gear teeth and the walls of the gear cavity and moved along the periphery of the gear cavity until it reaches the point at which the gear teeth engage. This action sets up a pressure differential between the liquid inlet and the liquid outlet causing liquid flow.

Such gears intermesh with their teeth to produce high local shear forces to form an emulsions. Gear pumps are preferred pumps to create the shear stress in a closed chamber without creation of air/liquid interfaces that are detrimental to the stability of sensitive active ingredient as proteins and peptides.

Preferably a pump having a magnetic drive is used for aseptic manufacture of microparticles. The pump head is coupled with the driving pump and can be easily removed for sterilization. A magnetic drive pump may have an outer annular magnet turned or rotated by a motor. An annular inner magnet may be disposed within the outer magnet and may be carried on a pump shaft. The inner magnet may be isolated from the outer magnet by a thin metallic or plastic cup. The inner magnet of such pumps may include a magnet and flux ring assembly which operates in the liquid that is moved through a system by the pump.

The gear pump may have suction shoes of the type shown in U.S. Pat. No. 4,127,365 the edge of the shoe fitting within the groove in each gear and bearing against the bottom of the groove. The shoe may form a passageway from the liquid inlet duct in the gear block (which is covered by the shoe) to the mesh point of the gear teeth. The shoe may fit over the mesh point of the gears and at least a span of two teeth to either side thereof, also fitting over the inlet duct and thus isolating this area from the main pump cavity to establish a small pump chamber within the pump cavity. Since there is a pressure differential when the pump is operating which is lower on the underside of the shoe than in the main pump cavity, the shoe is held against the pump block. The shoe separates the inlet duct from the discharge pressure, while accepting fluid flow.

The technology of gear pumps using magnetic drives is disclosed e.g. in U.S. Pat. Nos. 4,414,523 and 6,007,312. Gear pumps are disclosed e.g. in U.S. Pat. Nos. 4,846,641, 4,414,523, 5,702,234, 5,908,067, 4,493,625, 6,007,312 and 6,033,193. The contents of these patent specification are hereby incorporated by reference.

Such pumps may be the Micropump Ismatex brand obtained e.g. from Ismatec AG, Germany or Allschwil, Basel Switzerland. A typical model is IP65

Typical flow rates may be e.g from about 1 ml/min to about 12000 ml/min e.g 300 ml/min Typical drive speeds may be e.g from about 60 rpm to about 6000 rpm e.g 3000 rpm Typical differential pressures may be e.g from about 0.1 to about 5.2 bar (75 psi).

The present invention provides the unforeseen use of gear pumps to form emulsions. Using gear pumps emulsions may be formed in an aseptic environment.

Emulsion (d) is subsequently mixed with water (c) whilst stirring at high speed to form a water in oil in water emulsion. The water may contain stabilisers, for example polyvinyl alcohol or gelatin and buffers. The amount of stabilisers may be 0.01 to 20%, preferably 0.01 to 10% by weight, based on the aqueous solution of the stabiliser. Advantageously this emulsion step is carried out using a static mixer.

Using a static mixer, e.g a static laminar mixing device homogenization may be effected by the flow through the mixer. Generally, these devices have been built up of the so-called static mixer elements. These elements may be present to upset the flow of the liquids and mix them. Shear forces may be determined by the number and type of mixing elements and by the flow of liquids through the static mixer.

Such laminar mixers may be employed in mixing devices for the mixing of low-viscosity soluble additives to high-viscosity liquids. During mixing, the lower-viscosity (limpid) liquid may be fed to the main flow of the higher-viscosity (viscid) liquid, e.g., via a tube which may be arranged before or directly at the inlet to the mixer.

We have found that using a static mixer emulsions and microparticles having a controlled, predictable, and narrow cell size distribution may be obtained.

Energy required for liquid flow may be produced by pumps or the like.

A typical mixer is Sulzer Mixer SMXS DN6 obtainable from Sulzer AG, Winterthur, Switzerland.

Typical flow rates of the first liquid (e.g. the internal phase) containing the organic solvent may be e.g from about 1 ml/min to about 12000 ml/min e.g 20 ml/min.

Typical flow rates of the second liquid (e.g. the continuous phase) containing water may be e.g from about 1 ml/min to about 12000 ml/min e.g 400 ml/min Typical pressure drops may be e.g from about 0.1 to about 5.2 bar (75 psi)

Process steps b) to f) are preferably carried out at room temperature.

Removal of the organic solvent is advantageously undertaken with further stirring and by applying a vacuum. Heating can mean a temperature of up to ca. 60° C.

The microparticles may optionally be washed to purify them (to remove organic solvent and surfactants such as polyvinyl alcohol or gelatin) and then isolated by sedimentation or optionally by filtration and dried to remove water and any residual solvents. The known freeze-drying process is an especially suitable process for this.

Process step f) may be replaced by cross-flow filtration. Cross-flow filtration affords the circulation of the microparticle suspension tangentially to a membrane e.g. a polymer membrane (Polyethersulfone Pall membrane type Omega), e.g. a ceramic membrane, e.g. hollow fibers or e.g. spiral wound systems. The pore size of these membranes may be from 0.1 to 1 micrometer, preferably 0.8 micrometer for microfiltration. For ultrafiltration, membranes with molecular weight cut off ranging from 100 to 1,000,000 daltons are used. The suspension is recirculated until organic solvents and surfactants as e.g. polyvinyl alcohol or e.g. gelatin are removed. Microparticles may collected by sedimentation or by filtration.

We have found that microparticles therefrom having a controlled, predictable, and narrow cell size distribution may be obtained.

Typical flow rates tangentially over the membrane are e.g. from about 1 ml/min to about 100, 000 ml/min e.g. 15,000 ml/min Typical pressure drops may be e.g. from about 0.01 to about 5 bars.

After drying, microparticles are obtained in the form of free-flowing powders, which can be easily handled and further processed. The microparticles are essentially free from agglomerates.

Microparticles may be resuspended in an aqueous solution containing a bulking agent (e.g. mannitol or sucrose). This suspension may be freeze-dried to get lyophilized microparticles with advantageous storage properties.

The structure of the microparticles depends mainly on the preparation process, the consistency of the active ingredients or their solutions, and the choice of polymers or polymer mixtures.

Encapsulation of solid active ingredients and of active ingredients dispersed in polymer solutions leads to essentially compact particles with little to no porosity. Release of the active ingredient in contact with a physiological medium is determined in the case of such particles by the decomposition of the polymer. Release can be accelerated by adding water-soluble polymers, since porous structures can be formed through the dissolving of water-soluble polymers. The surface-active substance then protects the active ingredient, so that a delayed release of active ingredient remains assured.

Using the water in oil in water process, an aqueous solution containing the active ingredient is emulsified in the polymer solution. After drying, the water contained in droplets of this primary emulsion are removed and the previous droplets form then cavities in the dried polymer matrix. The cavities are distributed randomly throughout the volume. The size of the cavities distributed throughout the volume depends on the particle size, the process parameters, the selected polymers, their quantitative composition, and the type and amount of surface-active substance. The diameter of the cavities may be, for example, from 0.01 to 100 µm, depending on the size of the microparticles. The cavities are partially or wholly filled with an aqueous, solution of at least one pharmacologically active ingredient. The microparticles may have pores in the surface area, especially if water-soluble polymers are used concurrently during preparation, or if solutions, emulsions and dispersions of active ingredient are not fully encapsulated in the surface area.

The microparticles according to the invention are notable for the delayed release behaviour of the pharmaceutical active ingredient in a physiological medium. An initially excessive release (also called initial burst) and a subsequent complete breakdown of the release of active ingredient is not observed, even if surface-active peptides, polypeptides or proteins are used. The delayed release of active ingredient in, for example, blood plasma, can be maintained until the pharmacologically active ingredient in the particles has been used up, which can last for several days up to 12 months, depending on the amount and especially on the polymer used. In a first and second stage, the release of active ingredient may be essentially constant, whereby in the first stage a higher amount, for example 10 to 70% of the total amount of active ingredient, is delivered in a shorter space of time. With the type of composition and the amount of active ingredient in the particles, an optimum dosage can be set, which will suffice for long-term action with single or multiple administration. Using for example the starpolymer poly-D,L-lactide/glycolide the release of an active ingredient may last from several days up to 8 weeks. Using the starpolymer poly-D,L-lactide/glycolide together with interferon alpha 2b the invention provides a favourable release profile over at least 21 days. 10% to 60% of the active ingredient are released in the 2 to 5 days and the remaining active ingredient over a period of at least 21 days.

If the microparticles do not contain lecithin or phospholipid in the biologically degradable polymer, then in contrast to the particles according to the invention, no active ingredient is delivered after the initial burst phase. If a water-soluble polymer is additionally incorporated in the polymer matrix consisting of biologically degradable polymer and lecithin or phospholipid, then the active substance is released faster due to the creation of additional pores in the polymer matrix. The release period is then shortened and the release process is then essentially based on diffusion and not on a combination of diffusion and polymer degradation.

The microparticles according to the invention are suitable for formulating in solid, pasty and liquid formulations for oral application (tablet, coated tablet, capsule, drinking solution or suspension), for parenteral application (syringes for intravenous or intramuscular administration, infusion with suspensions), suppositories for rectal or vaginal application, aerosols for application by inhalation, powders, creams, gels and transdermal systems for subcutaneous application, and drops for nasal or ophthalmic application.

Following is a non-limiting description by way of example.

A) PREPARATION EXAMPLES

Example A1

Preparation of Microparticles a) Preparation of the Active Ingredient Solution 216.36 mg of recombinant human interferon alpha-2b and 43.27 mg of glycine are dissolved in 3 ml of a phosphate buffer (pH 7.5, 25 mM potassium and sodium hydrogen phosphates, 130 mM NaCl, 0.3 mM ethylenediamine tetraacetic acid).

b) Preparation of the Polymer Solution 2561.5 mg of copolycondensate of D,L-lactic acid and glycolic acid (50:50), 640.4 mg of polyvinyl pyrrolidone (PVP K12) and 865.4 mg of lecithin (Epikuron® 200) are dissolved in 20 ml of methylene chloride.

c) Preparation of the Aqueous Phase 40 g of polyvinyl alcohol (PVA Mowiol® 18-88) in phosphate buffer (1/15 M, pH 7.4, 7.24 g $KH_2PO_4$ and 30.28 g $Na_2HPO_4$) are dissolved in 4 litres of water at 20° C.

d) Preparation of the Primary Emulsion

Solutions a) and b) are emulsified for 10 minutes using a gear pump (Ismatec® MCP-Z, pump head P1830) at 200 rpm and at a pump capacity of 270 ml per minute.

e) Preparation of Microparticles

The primary emulsion is pumped by a gear pump (Ismatec® MCP-Z, pump head P1830) at 200 rpm and at a pump capacity of 20 ml per minute, and the aqueous phase is pumped by a gear pump (Ismatec® MCP-Z, pump head P130) at 575 rpm and at a pump capacity of 400 ml per minute in a mixing vessel (Statischemischer® SMXS DN6)

f) Methylene Chloride is Evaporated Whilst Stirring.

g) The microparticles are filtered off, dried in a vacuum, and the pre-dried microparticles undergo freeze-drying. A free-flowing powder consisting of microparticles with an average diameter of 60-70 μm is obtained.

Example A2

Preparation of Microparticles

The procedure of example A1 is followed using the following solutions:

a) Preparation of the Active Ingredient Solution 216.36 mg of recombinant human interferon alpha-2b and 43.27 mg of glycine are dissolved in 2 ml of a phosphate buffer (pH 7.5, 25 mM potassium and sodium hydrogen phosphates, 130 mM NaCl, 0.3 mM ethylenediamine tetraacetic acid).

b) Preparation of the Polymer Solution 2134.6 mg of copolycondensate of D,L-lactic acid and glycolic acid (50:50), 1067.3 mg of polyvinyl pyrrolidone (PVP K12) and 865.4 mg of lecithin (Epikuron® 200) are dissolved in 20 ml of methylene chloride.

c) Preparation of the Aqueous Phase 40 g of polyvinyl alcohol (PVA Mowiol® 18-88) in phosphate buffer (1/15 M, pH 7.4, 7.24 g $KH_2PO_4$ and 30.28 g $Na_2HPO_4$) are dissolved in 4 litres of water at 20° C.

Steps d to g are carried out as described in example A1.

A free-flowing powder consisting of microparticles with an average diameter of 60-70 μm is obtained.

Example A3

Preparation of Microparticles

The procedure of example A1 is followed using the following solutions:

a) Preparation of the Active Ingredient Solution 50.6 mg of recombinant human interferon alpha-2b and 10.12 mg of glycine are dissolved in 3 ml of a phosphate buffer (pH 7.5, 25 mM potassium and sodium hydrogen phosphates, 130 mM NaCl, 0.3 mM ethylenediamine tetraacetic acid).

b) Preparation of the Polymer Solution 2000 mg of copolycondensate of D,L-lactic acid and glycolic acid (50:50), 2000 mg of polyvinyl pyrrolidone (PVP K12) and 1000 mg of lecithin (Epikuron® 200) are dissolved in 20 ml of methylene chloride.

c) Preparation of the Aqueous Phase 40 g of polyvinyl alcohol (PVA Mowiol® 18-88) in phosphate buffer (1/15 M, pH 7.4, 7.24 g $KH_2PO_4$ and 30.28 g $Na_2HPO_4$) are dissolved in 4 litres of water at 20° C.

Steps d to g are carried out as described in example A1.

A free-flowing powder consisting of microparticles with an average diameter of 60-70 μm is obtained.

Example A4

Preparation of Microparticles: Adjustment of the Osmolarity of the Aqueous Outer Phase a) Preparation of the Active Ingredient Solution 216.36 mg of recombinant human interferon alpha-2b and 43.27 mg of glycine are dissolved in 3 ml of a phosphate buffer (pH 7.5, 25 mM potassium and sodium hydrogen phosphates, 130 mM NaCl, 0.3 mM ethylenediamine tetraacetic acid).

b) Preparation of the Polymer Solution 2561.5 mg of copolycondensate of D,L-lactic acid and glycolic acid (50:50), 640.4 mg of polyvinyl pyrrolidone (PVP K12) and 865.4 mg of lecithin (Epikuron® 200) are dissolved in 20 ml of methylene chloride.

c) Preparation of the Aqueous Phase 40 g of polyvinyl alcohol (PVA Mowiol® 18-88) in phosphate buffer (1/15 M, pH 7.4, 7.24 g $KH_2PO_4$ and 30.28 g $Na_2HPO_4$) are dissolved in 4 litres of water at 20° C. The osmolarity of the solution is then adjusted with mannitol to the osmolarity of the protein aqueous solution a) at about 600 mOsm.

d) Preparation of the Primary Emulsion

Solutions a) and b) are emulsified for 10 minutes using a gear pump (Ismatec® MCP-Z, pump head P1830) at 200 rpm and at a pump capacity of 270 ml per minute.

e) Preparation of Microparticles

The primary emulsion is pumped by a gear pump (Ismatec® MCP-Z, pump head P1830) at 200 rpm and at a pump capacity of 20 ml per minute, and the aqueous phase is pumped by a gear pump (Ismatec® MCP-Z, pump head P130) at 575 rpm and at a pump capacity of 400 ml per minute in a mixing vessel (Statischemischer® SMXS DN6).

f) Methylene Chloride is Evaporated Whilst Stirring.

g) The microparticles are washed by using different cycle of sedimentation/soak-up of supernatant/addition of fresh water (filtration and washing on the filter could be an alternative), the washed microparticles can be freeze dried as a suspension or as powder after filtration. A free-flowing powder consisting of microparticles with an average diameter of 60-70 μm is obtained. For washing and freeze-drying the microparticles are suspended in the buffered solution and filled in vials as suspension prior to lyophilization. The buffered solution is the solution used for the aqueous solution c) is used without the polyvinylalcohol or any other surface active agents:

A phosphate buffer (1/15 M, pH 7.4, 7.24 g $KH_2PO_4$ and 30.28 g $Na_2HPO_4$) is prepared in 4 litres of water at 20° C. The osmolarity of the solution is then adjusted with Mannitol to the osmolarity of the protein aqueous solution a) at about 600 mOsm.

Example A5

Preparation of Microparticles: Use of the Cross-Flow Filtration Technology to Wash the Microparticles Suspension a) Preparation of the Active Ingredient Solution 216.36 mg of recombinant human interferon alpha-2b and 43.27 mg of glycine are dissolved in 3 ml of a phosphate buffer (pH 7.5, 25 mM potassium and sodium hydrogen phosphates, 130 mM NaCl, 0.3 mM ethylenediamine tetraacetic acid).

b) Preparation of the Polymer Solution 2561.5 mg of copolycondensate of D,L-lactic acid and glycolic acid (50:50), 640.4 mg of polyvinyl pyrrolidone (PVP K12) and 865.4 mg of lecithin (Epikuron® 200) are dissolved in 20 ml of methylene chloride.

c) Preparation of the Aqueous Phase 40 g of polyvinyl alcohol (PVA Mowiol® 18-88) in phosphate buffer (1/15 M, pH 7.4, 7.24 g $KH_2PO_4$ and 30.28 g $Na_2HPO_4$) are dissolved in 4 litres of water at 20° C.

d) Preparation of the Primary Emulsion

Solutions a) and b) are emulsified for 10 minutes using a gear pump (Ismatec® MCP-Z, pump head P1830) at 200 rpm and at a pump capacity of 270 ml per minute.

e) Preparation of Microparticles

The primary emulsion is pumped by a gear pump (Ismatec® MCP-Z, pump head P1830) at 200 rpm and at a pump capacity of 20 ml per minute, and the aqueous phase is pumped by a gear pump (Ismatec® MCP-Z, pump head P130) at 575 rpm and at a pump capacity of 400 ml per minute in a mixing vessel (Statischemischer® SMXS DN6).

f) The whole microparticle suspension recovered in a tank is then washed by mean of the cross-flow filtration technology to remove methylenechloride and all the salts and excipients contained in the aqueous outer phase c): the microparticle suspension is pumped in a loop and allowed to circulate tangentially to a polymer membrane with a pore size of 0.8 micrometer e.g. polyethersulfone with low binding properties or e.g. ceramic membranes. The methylenechloride, salts and excipients are removed through the membrane by mean of the diafiltration mode of the cross-flow filtration. They are filtered and removed as permeat whereas the microparticles that cannot pass through the membrane stay in suspension and come back in the loop as retentat. The water containing methylenechloride, salts and excipients as PVA that is removed with the permeat is replaced continuously by fresh water in order to keep the volume of the initial microparticles suspension at a constant level.

g) Microparticles are filtered off, dried in a vacuum, and the pre-dried microparticles undergo freeze-drying. The microparticles suspension can as well be concentrated and fill in vial as suspension prior to freeze-drying. A free-flowing powder consisting of microparticles with an average diameter of 60-70 μm is obtained.

B) APPLICATION EXAMPLES

Example B1

In Vitro Drug Release 50 mg of the microparticles according to example A1 are added to a phosphate buffer (pH 7.4, 1/15 M, pH 7.4, 7.24 g $KH_2PO_4$ and 30.28 g $Na_2HPO_4$) and the mixture is maintained at 37° C. Then, at certain intervals, the interferon alpha-2b content in the phosphate buffer is determined. The results are listed in table 1.

TABLE 1

| time (days) | content in the buffer (mg) | cumulative content in the buffer (mg) |
|---|---|---|
| 1 | 0.75995 | 0.75995 |
| 2 | 0.43124 | 1.19119 |
| 3 | 0.28770 | 1.47889 |
| 6 | 0.34728 | 1.82617 |
| 8 | 0.19125 | 2.01742 |
| 10 | 0.13053 | 2.14795 |
| 14 | 0.11585 | 2.26380 |
| 17 | 0.07464 | 2.33844 |
| 21 | 0.06015 | 2.39859 |

Example B2

The process is carried out according to example B1 with the microparticles according to example A2. The results are listed in table 2.

TABLE 2

| time (days) | content in the buffer (mg) | cumulative content in the buffer (mg) |
|---|---|---|
| 1 | 1.03206 | 1.03206 |
| 2 | 0.45725 | 1.48931 |
| 3 | 0.19730 | 1.68661 |
| 6 | 0.17711 | 1.86372 |
| 8 | 0.13755 | 2.00147 |
| 10 | 0.11351 | 2.11498 |
| 14 | 0.15434 | 2.26932 |
| 17 | 0.09404 | 2.36336 |
| 21 | 0.06710 | 2.430046 |

What is claimed is:

1. A process for producing microparticles comprising the steps of:

a) dissolving at least one polypeptide in an aqueous buffer to produce an active ingredient solution,
b) dissolving a biologically degradable polymer, a water-soluble polymer, and lecithin in an organic solvent to produce a polymer solution containing about 20% lecithin,
c) mixing a water-soluble polymer with an aqueous buffer to form an aqueous solution,
d) mixing the active ingredient solution of a) and the polymer solution of b) using a gear pump to form an emulsion,
e) pumping the emulsion of d) and the aqueous solution of c) with a gear pump to a static mixer and mixing the same in the static mixer to form a water in oil in water emulsion,
f) removing the solvent from the emulsion of e), and
g) separating the microparticles by filtering and freeze-drying,
wherein the microparticles do not exhibit an initial burst release of the therapeutic polypeptide contained therein.

2. The process according to claim 1 wherein the solvent is removed from the microparticles using cross-filtration technology by:
a) circulating emulsion e) tangentially to a membrane at a constant flow wherein methylenehloride, salts and excipients are removed through the membrane,
b) replacing the water removed through the membrane by fresh water, and
c) separating the microparticles by filtering and freeze-drying.

3. The process of claim 1 wherein the aqueous buffer is a phosphate buffer.

4. The process of claim 1 wherein the organic solvent is methylenechloride.

5. The process of claim 1 wherein the surfactant is polyvinyl alcohol.

6. The process of claim 1 wherein the removing of step t) is performed by evaporation.

7. The process of claim 1 wherein the amount of phospholipid or lecithin is from 0.01 to 90% w/w of the final microparticle weight.

8. The process of claim 1 wherein the biologically degradable polymer is selected from the group consisting of a polycarbonate; a polyester of an aliphatic hydroxycarboxylic acid; a polyester of an aminocarboxylic acid; a polyamide of an aliphatic hydroxycarboxylic acid; a polyamide of an aminocarboxylic acids; a homo-condensate of α-hydroxycarboxylic acid; a copolycondensate of α-hydroxycarboxylic acid; glycolic acid; lactic acid; poly-L-lactic acid; poly-D,L-lactic acid; a copolycondensate of poly-D,L-lactide/glycolide with a monomer ratio selected from the group consisting of 10:1 to 1:10, 1:4 to 4:1, and 1:1, and a molecular weight of 5000 to 100,000 daltons; and mixtures thereof.

9. The process of claim 8 wherein the biologically degradable polymer is a copolycondensate of D,L-lactic acid and glycolic acid (1:1).

10. The process of claim 2 wherein the membrane is selected from the group consisting of a polymer membrane, ceramic membrane, hollow fiber, and spiral wound system.

11. A microparticle prepared by the process of claim 1, the microparticle comprising
a) at least one biologically degradable polymer,
b) optionally at least one water soluble polymer,
c) at least one pharmacologically active ingredient distributed in the biologically degradable polymer, and
d) a phospholipid or lecithin.

12. A microparticle according to claim 11 wherein the amount of phospholipid or lecithin is from about 0.01 to about 90%, preferably from about 0.1 to about 70%, most preferably from about 0.1 to about 20% w/w of the final MP weight.

13. A microparticle according to claim 11, which have a diameter of 0.1 to 200 μm.

14. A microparticle according to claim 11, in which the biologically degradable polymer comprises homo- or copolyester of dicarboxylic acid, alkylene diol, polyalkylene glycol and/or aliphatic hydroxycarboxylic acid; homo- or copolyamide of dicarboxylic acids, alkylene diamine and/or aliphatic aminocarboxylic acid; corresponding polyester-polyamide copolymer; polyanhydride; polyorthoester; polyphosphazene; and polycarbonates.

15. A microparticle according to claim 14, in which the polymer is poly-L- or poly-D,L-lactic acid or poly-D,L-lactide/glycolide with a monomer ratio of ca. 1:1 and a molecular weight of 5000 to 100,000 daltons.

16. A microparticle according to claim 15 comprising optionally at least one water-soluble polymer.

17. A microparticle according to claim 16, wherein the water-soluble polymer is polyvinyl pyrrolidone.

18. A microparticle according to claim 11, in which the amount of biologically degradable polymers is 99 to 1% by weight, and the amount of water-soluble polymers is 1 to 99% by weight, based on the composition of the polymers.

19. A microparticle according to claim 11, in which the phospholipid is phosphatidyl choline.

20. A microparticle according to claim 11, in which the active ingredients are peptides, polypeptides and proteins.

21. A microparticle according to claim 20, in which the active ingredients are antibodies, growth hormones, insulin, interferons, erythropoietin, calcitonin, heparin, somatostatins, cell-stimulating factors and parathyroid hormones.

22. A microparticle according to claim 21 wherein the interferon is interferon alpha 2b.

23. A microparticle according to claim 11, which contain 1 to 20% by weight active ingredient, based on the weight of the microparticles.

* * * * *